(12) United States Patent
Locke et al.

(10) Patent No.: US 11,896,464 B2
(45) Date of Patent: Feb. 13, 2024

(54) METHOD TO DYNAMICALLY MEASURE APPOSITION AND PATIENT LIMB MOVEMENT IN A NEGATIVE PRESSURE CLOSED INCISION DRESSING

(71) Applicant: KCI LICENSING, INC., San Antonio, TX (US)

(72) Inventors: Christopher Brian Locke, Bournemouth (GB); Justin Alexander Long, Lago Vista, TX (US); Timothy Mark Robinson, Blandford Forum (GB)

(73) Assignee: KCI Licensing, Inc., San Antonio, TX (US)

( * ) Notice: Subject to any disclaimer, the term of this patent is extended or adjusted under 35 U.S.C. 154(b) by 140 days.

(21) Appl. No.: 17/045,956

(22) PCT Filed: Apr. 8, 2019

(86) PCT No.: PCT/US2019/026375
§ 371 (c)(1),
(2) Date: Oct. 7, 2020

(87) PCT Pub. No.: WO2019/199687
PCT Pub. Date: Oct. 17, 2019

(65) Prior Publication Data
US 2021/0023281 A1 Jan. 28, 2021

Related U.S. Application Data

(60) Provisional application No. 62/657,325, filed on Apr. 13, 2018.

(51) Int. Cl.
*A61M 1/00* (2006.01)
*A61F 13/00* (2006.01)

(52) U.S. Cl.
CPC .. *A61F 13/00051* (2013.01); *A61F 13/00068* (2013.01); *A61M 1/73* (2021.05);
(Continued)

(58) Field of Classification Search
CPC ............ A61M 1/90; A61M 2205/0283; A61M 2205/15; A61M 2205/18;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Adam Marcetich
*Assistant Examiner* — Rachel O'Connell

(57) ABSTRACT

A negative pressure wound therapy system includes at least one sensor coupled to a wound dressing for a wound of a patient, and a control circuit. The at least one sensor is configured to output an indication of a displacement of the wound dressing. The control circuit is configured to receive the indication of the displacement of the wound dressing, calculate a therapy parameter corresponding to the indication of the displacement, and output the therapy parameter.

17 Claims, 7 Drawing Sheets

(52) U.S. Cl.
CPC .............. *A61M 1/74* (2021.05); *A61M 1/915* (2021.05); *A61M 1/966* (2021.05); *A61M 1/984* (2021.05); *A61M 2205/0283* (2013.01); *A61M 2205/15* (2013.01); *A61M 2205/18* (2013.01); *A61M 2205/332* (2013.01); *A61M 2205/3334* (2013.01); *A61M 2205/3379* (2013.01); *A61M 2205/3553* (2013.01); *A61M 2230/63* (2013.01)

(58) Field of Classification Search
CPC .... A61M 2205/332; A61M 2205/3334; A61M 2205/3379; A61M 2205/3553; A61M 2230/63; A61F 13/00068
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,989,075 B1* | 1/2006 | Kao | A61K 8/0208 162/123 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0022990 A1* | 1/2010 | Karpowicz | G06Q 20/127 604/543 |
| 2014/0005618 A1* | 1/2014 | Locke | A61M 1/732 604/319 |
| 2016/0015311 A1* | 1/2016 | Jiang | G01L 5/164 600/592 |
| 2017/0128272 A1 | 5/2017 | Wu et al. | |
| 2017/0176167 A1* | 6/2017 | Keller | G01L 1/225 |
| 2017/0361045 A1* | 12/2017 | Fu | A61M 16/16 |
| 2018/0021178 A1* | 1/2018 | Locke | A61M 1/962 602/43 |
| 2018/0042521 A1* | 2/2018 | Ryu | A61F 13/53 |
| 2018/0060520 A1* | 3/2018 | Degen | G16H 80/00 |
| 2020/0253539 A1* | 8/2020 | Kaikenger | G01L 1/205 |
| 2022/0008237 A1* | 1/2022 | Mirza | G06N 20/00 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |

(56) References Cited

FOREIGN PATENT DOCUMENTS

| | | | |
|---|---|---|---|
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2007/030598 A2 | 3/2007 | |
| WO | WO-2007/030601 A2 | 3/2007 | |
| WO | WO-2009/093116 A1 | 7/2009 | |
| WO | WO-2009093116 A1 * | 7/2009 | .......... A61M 1/0031 |
| WO | WO-2010/053870 A1 | 5/2010 | |
| WO | WO-2014/140578 A1 | 9/2014 | |
| WO | WO-2018/033794 A1 | 2/2018 | |
| WO | WO-2018033794 A1 * | 2/2018 | ....... A61F 13/00068 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.
International Search Report and Written Opinion in International Application No. PCT/US2019/026375, dated Sep. 9, 2019.

\* cited by examiner

METHOD TO DYNAMICALLY MEASURE APPOSITION AND PATIENT LIMB MOVEMENT IN A NEGATIVE PRESSURE CLOSED INCISION DRESSING

CROSS-REFERENCE TO RELATED APPLICATIONS

This application claims the benefit of priority to international application PCT/US2019/026375, filed Apr. 8, 2019, and U.S. Provisional Application No. 62/657,325, filed on Apr. 13, 2018, the complete disclosures of which are hereby incorporated herein by reference in their entireties.

BACKGROUND

The present disclosure relates generally to wound therapy systems and devices, and more particularly to systems and methods for dynamically measuring apposition and patient limb movement in a negative pressure closed incision dressing.

Negative pressure wound therapy (NPWT) is a type of wound therapy that involves applying negative pressure (relative to atmosphere pressure) to a wound site, via a wound dressing, to promote wound healing. Some NPWT systems include a pump which operates to maintain the wound site at negative pressure by removing wound exudate from the wound site via the wound dressing.

SUMMARY

One implementation of the present disclosure is a sensor system. the sensor system includes at least one sensor coupled to a wound dressing for a wound of a patient, and a control circuit. The at least one sensor is configured to output an indication of a displacement of the wound dressing. The control circuit is configured to receive the indication of the displacement of the wound dressing, calculate a therapy parameter corresponding to the indication of the displacement, and output the therapy parameter. The therapy parameter may include an appositional force or a moisture or hydration level.

In some embodiments, the therapy parameter includes at least one of an appositional force that the wound dressing applies to the wound of the patient or a movement of a joint of the patient about the wound dressing.

In some embodiments, the therapy parameter includes the appositional force, and the control circuit is further configured to calculate a difference between the appositional force and a target appositional force value and modify a pressure applied by the wound dressing to the wound to reduce the difference.

In some embodiments, the wound dressing is an incisional wound dressing for placement over a closed incision.

In some embodiments, the wound dressing includes a lower, wound facing layer, an elongate foam, and a cover layer for sealing the dressing to a patient's skin. The dressing can collapse under negative pressure and apply at least one of a lateral force or a longitudinal force.

In some embodiments, the at least one sensor includes a first electro active polymer (EAP) sensor configured to detect a latitudinal displacement and a second EAP sensor configured to detect a longitudinal displacement. The indication of a displacement of the wound dressing is based upon a change in the capacitance of at least one of the first EAP sensor or the second EAP sensor corresponding to the displacement of the wound dressing.

In some embodiments, the at least one sensor is removably attached to a surface of the wound dressing.

In some embodiments, the at least one sensor is disposed within the wound dressing.

In some embodiments, the control circuit is configured to compare the therapy parameter to a predetermined threshold condition including at least one of a minimum threshold or a maximum threshold, and output an alert responsive to the therapy parameter not satisfying the predetermined threshold condition.

In some embodiments, the sensor system includes a moisture sensor configured to detect a level of moisture in the wound dressing, and the control circuit is further configured to compare the level of moisture to a predetermined threshold moisture condition including at least one of a minimum moisture threshold or a maximum moisture threshold, and output an alert responsive to the level of moisture not satisfying the predetermined threshold moisture condition.

In some embodiments, the at least one sensor is configured to measure at least one of a fluid level or a fluid flow rate through the wound dressing.

In some embodiments, control circuit is coupled to a communications circuit, and the communications circuit is configured to transmit the therapy parameter to a remote electronic device.

Another implementation of the present disclosure is a method. The method includes receiving an indication of a displacement of a wound dressing for a wound of a patient from at least one electro-active polymer (EAP) sensor, the at least one EAP sensor coupled to the wound dressing, the at least one EAP sensor configured to output the indication based on a change in capacitance of the at least one EAP sensor corresponding to the displacement; calculating a therapy parameter corresponding to the indication of the displacement; and outputting the therapy parameter.

In some embodiments, the therapy parameter includes at least one of an appositional force that the wound dressing applies to the wound of the patient or a movement of a joint of the patient about the wound dressing.

In some embodiments, the therapy parameter includes the appositional force, and the method further includes calculating a difference between the appositional force to a target appositional force value and modifying a pressure applied by the wound dressing to the wound to reduce the difference.

In some embodiments, the at least one EAP sensor includes a first EAP sensor configured to detect a latitudinal displacement and a second EAP sensor configured to detect a longitudinal displacement.

In some embodiments, the method further includes receiving an indication of a level of moisture in the wound dressing from a moisture sensor, comparing the level of moisture to a predetermined threshold moisture condition including at least one of a minimum moisture threshold or a maximum moisture threshold, and outputting an alert responsive to the level of moisture not satisfying the predetermined threshold moisture condition.

In some embodiments, the method further includes transmitting the indication of the displacement to at least one of a negative pressure wound therapy device configured to apply a vacuum to the wound dressing or a remote electronic device. The indication of the displacement is transmitted to the remote electronic device, and the method further includes using the remote electronic device to perform at least one of outputting the indication of the displacement, calculating the therapy parameter, or outputting the therapy parameter, the therapy parameter being indicative of whether the patient is moving more or less than a desired movement subsequent to a surgery.

In some embodiments, the method further includes measuring, by the at least one EAP sensor, at least one of a fluid level or a fluid flow rate through the wound dressing.

Another implementation of the present disclosure is a non-transitory computer readable medium storing computer executable instructions which when executed by one or more processors cause the one or more processors to receive an indication of a longitudinal displacement of a wound dressing for a wound of a patient from at least one displacement sensor, the wound dressing defining a first length in a first direction and a second length in a second direction, the second length greater than the first length, the at least one displacement sensor coupled to the wound dressing, the longitudinal displacement corresponding to the second direction, the at least one displacement sensor configured to output the indication based on a change in capacitance of the at least one displacement sensor corresponding to the longitudinal displacement; calculate a therapy parameter corresponding to the indication of the displacement; and output the therapy parameter.

Another implementation of the present disclosure is a negative pressure wound therapy system. The negative pressure wound therapy system includes a therapy control and communication device including at least one pump configured to create a reduced pressure, a user interface, and a data communications interface. The negative pressure wound therapy system also includes a wound dressing sized and shaped for placement over a joint, the wound dressing including at least one sensor, the at least one sensor configured to detect a force on the wound dressing and to communicate with the data communications interface. The sensor is configured to determine when a joint is articulated.

Another implementation of the present disclosure is a method. The method includes detecting a force on a wound dressing by at least one sensor of a wound dressing, the wound dressing sized and shaped for placement over a joint; determining articulation of the joint based on the detected force; and communicating at least one of an indication of the detected force or an indication of the determined articulation to a data communications interface of a therapy control and communication device, the therapy control and communication device further including at least one pump configured to create a reduced pressure and a user interface.

In some embodiments, the method includes at least one of storing or outputting, by the therapy control and communication device, a count of received indications of the joint being articulated.

In some embodiments, the method includes transmitting, by the data communications interface, the count of received indications to a remote destination.

In some embodiments, the number of received indications is at least one of stored or outputted in association with a predetermined period of time during which the count of received indications was received, and the predetermined period of time is greater than or equal to an hour and less than or equal to a year.

In some embodiments, the method includes evaluating, by the therapy control and communication device, a compliance condition based on the count of received indications, the compliance condition including a corresponding threshold count of received indications, and outputting at least one of an indication of patient compliance responsive to the count of received indications satisfying the compliance condition or an indication of patient non-compliance responsive to the count of received indications not satisfying the compliance condition.

In some embodiments, the method includes increasing, by the therapy control and communication device, the threshold count of received indications in response to expiration of a second predetermined period of time, the second predetermined period of time being greater than or equal to a day and less than or equal to a week.

In some embodiments, outputting the indication of patient non-compliance includes transmitting the indication of patient non-compliance to at least one of a device associated with the patient or a device associated with a caregiver.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a negative pressure wound therapy (NPWT) device, associated sensor devices, and components thereof are shown, according to various exemplary embodiments. In some embodiments, an NPWT system includes at least one sensor coupled to a wound dressing for a wound of a patient, and a control circuit. The at least one sensor is configured to output an indication of a displacement of the wound dressing. The control circuit is configured to receive the indication of the displacement of the wound dressing, calculate a therapy parameter corresponding to the indication of the displacement, and output the therapy parameter. The therapy parameter may include an appositional force or a moisture or hydration level.

In some embodiments, the NPWT system can record data such as dressing force or appositional force, fluid or dressing hydration levels, and patient motion, including longitudinal motion and joint articulation. This data can be used to more frequently and accurately measure how a patient is undergoing therapy, which can enable a clinician to make better decisions regarding therapy regimens, and can enable the NPWT system to adjust the applied vacuum to more effectively deliver therapy to the patient. The NPWT system can be used to generate data enabling better surgical outcomes, including post-surgery incision healing and reduced rates of scarring/infection, by enabling more effective NPWT device operation and wound dressing manipulation. For example, the appositional force data can be used for closed-loop control of the negative pressure wound therapy applied by the NPWT system, allowing for therapy more targeted to clinical goals (namely, appositional force control) than existing pressure-based control systems.

Negative Pressure Wound Therapy System

Figure 1:
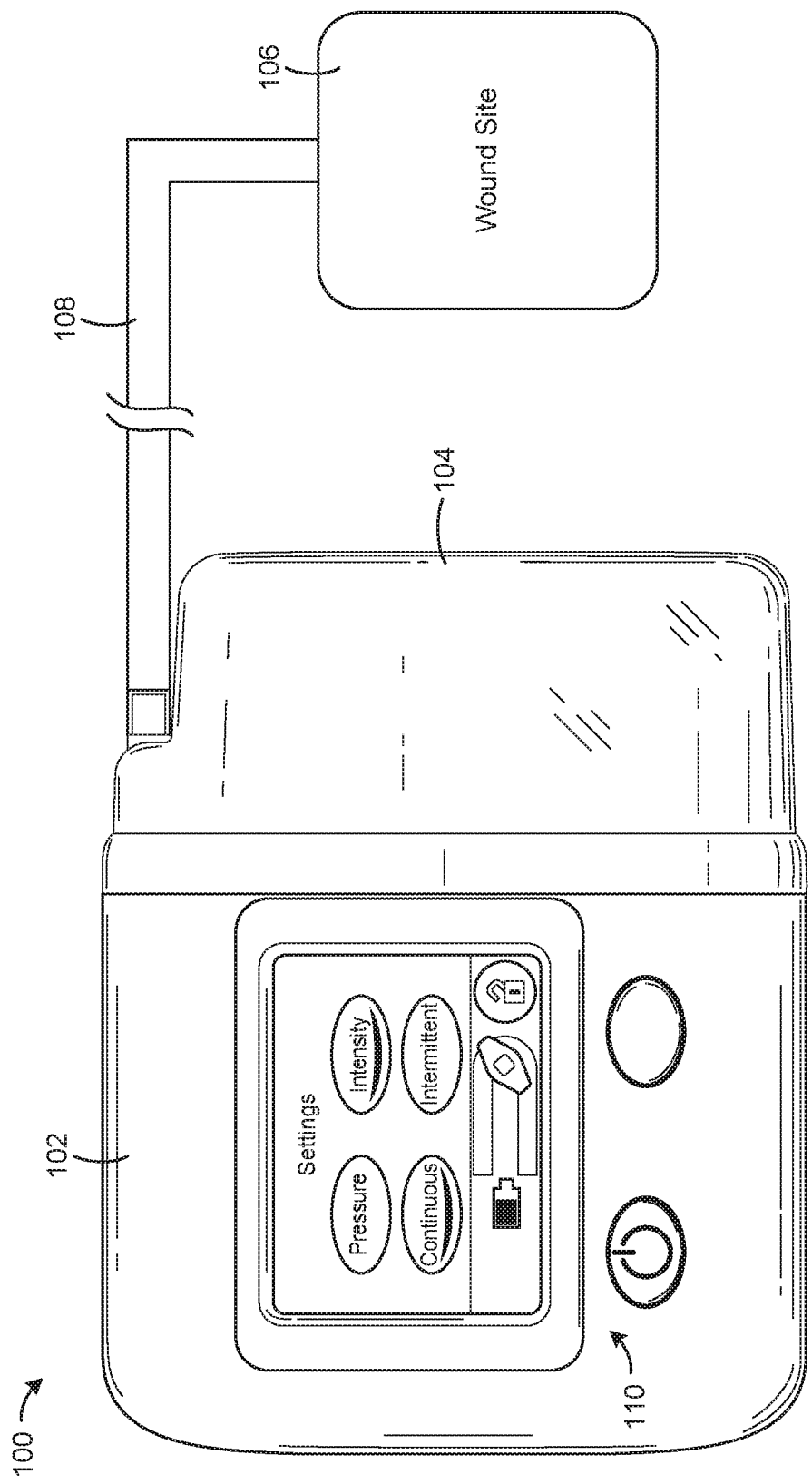
FIG. 1 is a drawing of a negative pressure wound therapy (NPWT) system including a NPWT device fluidly connected with a wound dressing at a wound site and a sensor system coupled to the wound dressing, according to an exemplary embodiment.
Figure 2:
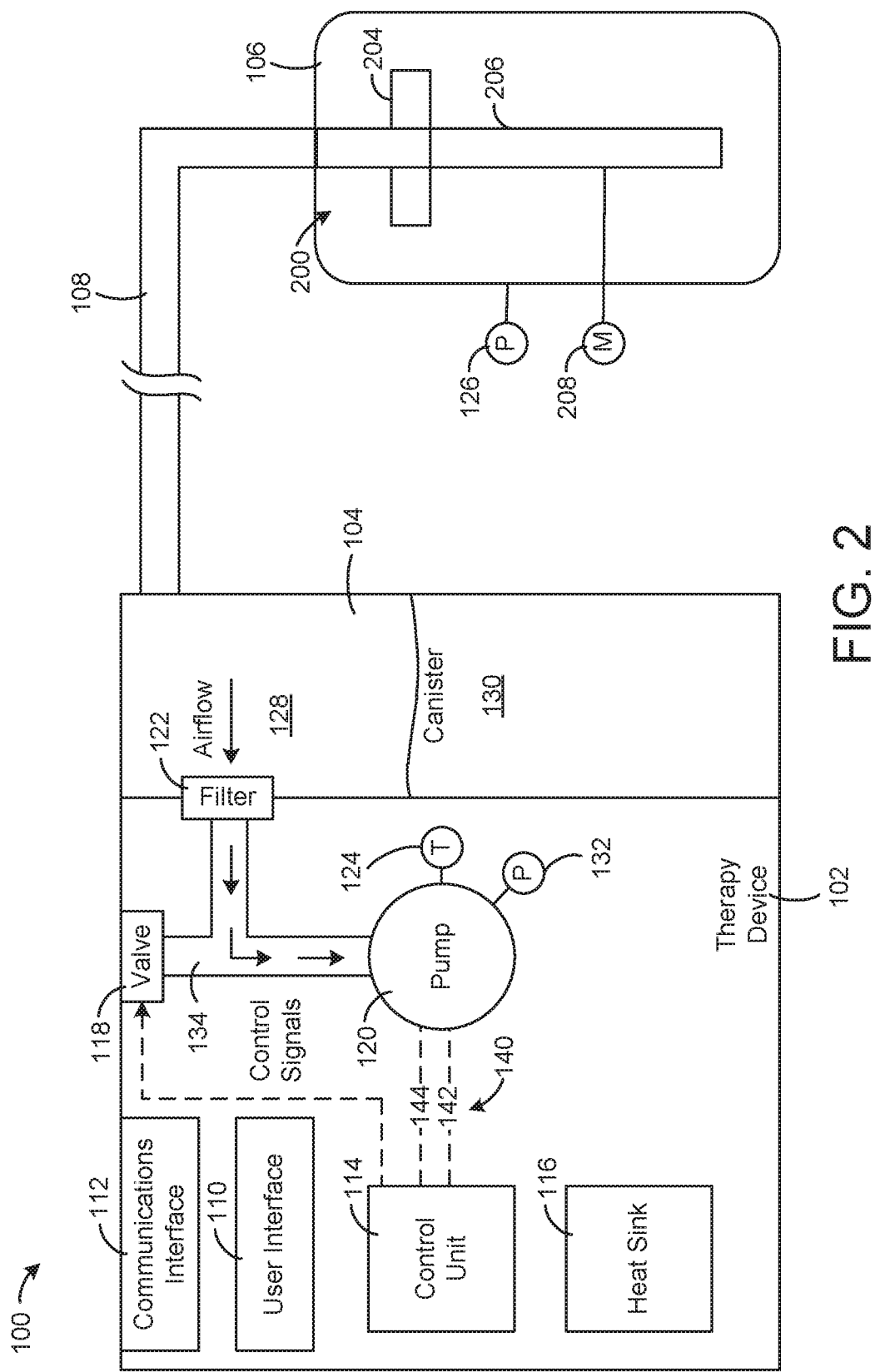
FIG. 2 is a block diagram illustrating the NPWT device and sensor system of FIG. 1 in greater detail, according to an exemplary embodiment.

Referring now to FIGS. 1-2, a negative pressure wound therapy (NPWT) system 100 is shown, according to an exemplary embodiment. NPWT system 100 is shown to include a therapy device 102 (e.g., a therapy control and communication device) fluidly connected to a wound site 106 via tubing 108. Wound site 106 may include a tissue wound as well as a wound dressing that covers the tissue wound and adheres to a patient's skin. Various embodiments of wound dressings are described with further reference to FIGS. 3-6. Several examples of wound dressings which can be used in combination with NPWT system 100 are also described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound site 106. Therapy device 102 can draw a vacuum at wound site 106 (relative to atmospheric pressure) by removing wound exudate, air, and other fluids from wound site 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 106 may include instillation fluid previously delivered to wound site 106. Instillation fluid can include, for example, a cleansing fluid, a prescribed fluid, a medicated fluid, an antibiotic fluid, or any other type of fluid which can be delivered to wound site 106 during wound treatment.

The fluids removed from wound site 106 pass through tubing 108 and are collected in canister 104, in some embodiments. Canister 104 may be a component of therapy device 102 configured to collect wound exudate and other fluids removed from wound site 106. In some embodiments, canister 104 is detachable from therapy device 102 to allow canister 104 to be emptied and replaced as needed. A lower portion 130 of canister 104 may be filled with wound exudate and other fluids removed from wound site 106, whereas an upper portion 128 of canister 104 may be filled with air. Therapy device 102 can be configured to draw a vacuum within canister 104 by pumping air out of canister 104. The reduced pressure within canister 104 can be translated to wound site 106 via tubing 108 such that wound site 106 is maintained at the same pressure as canister 104.

Referring particularly to FIG. 2, a block diagram illustrating therapy device 102 in greater detail is shown, according to an exemplary embodiment. Therapy device 102 is shown to include a pump 120, a filter 122, a valve 118, a heat sink 116, and a control unit 114. Pump 120 can be fluidly coupled to canister 104 (e.g., via conduit 134) and can be configured to draw a vacuum within canister 104 by pumping air out of canister 104. In some embodiments, pump 120 is configured to operate in both a forward direction and a reverse direction. For example, pump 120 can operate in the forward direction to pump air out of canister 104 and decrease the pressure within canister 104. Pump 120 can operate in the reverse direction to pump air into canister 104 and increase the pressure within canister 104. Pump 120 can be controlled by control unit 114, described in greater detail below. Pump 120 can create a reduced pressure (e.g., to be applied to wound dressing 214).

Pump 120 is a piezoelectric pump. In some embodiments, the pump 120 includes a movable member (e.g., diaphragm) which undergoes mechanical displacement based on a voltage applied to the movable member, such as by oscillating in response to receiving an alternating current. By oscillating, the movable member can push air to generate the negative pressure applied by the pump 120. The movable member can be metallic. Pump 120 can include a copper disc with a slit which opens when pushed by the movable member. In some embodiments, the movable member oscillates at approximately 21 kHz. Under typical operational conditions, the pump 120 can operate silently or near silently. For example, noise generated by pump 120 can be less than a noise threshold which can be heard by a typical user. In an embodiment, pump 120 is a Vacuum Pump manufactured by Koge Micro Tech Co., Ltd.

In some embodiments, NPWT system 100 includes a plurality of pumps 120. For example, therapy device 102 may include multiple pumps 120, each coupled to tubing 108 and controlled by control unit 114. NPWT system 100 may include a plurality of therapy devices 102, each of which may include one or more pumps 120.

Filter 122 can be positioned between canister 104 and pump 120 (e.g., along conduit 134) such that the air pumped out of canister 104 passes through filter 122. Filter 122 can be configured to prevent liquid or solid particles from entering conduit 134 and reaching pump 120. Filter 122 may include, for example, a bacterial filter that is hydrophobic and/or lipophilic such that aqueous and/or oily liquids will bead on the surface of filter 122. Pump 120 can be configured to provide sufficient airflow through filter 122 that the pressure drop across filter 122 is not substantial (e.g., such that the pressure drop will not substantially interfere with the application of negative pressure to wound site 106 from therapy device 102).

Valve 118 can be fluidly connected with pump 120 and filter 122 via conduit 134. In some embodiments, valve 118 is configured to control airflow between conduit 134 and the environment around therapy device 102. For example, valve 118 can be opened to allow airflow between conduit 134 and the environment around therapy device 102, and closed to prevent airflow between conduit 134 and the environment around therapy device 102. Valve 118 can be opened and closed by control unit 114, described in greater detail below. When valve 118 is closed, pump 120 can draw a vacuum within conduit 134 and canister 104 by causing airflow through filter 122 in a first direction, as shown in FIG. 2. When valve 118 is open, airflow from the environment around therapy device 102 may enter conduit 134 and fill the vacuum within conduit 134 and canister 104.

While FIG. 2 illustrates the use of the canister 104 and filter 122, it will be appreciated that in some embodiments, the therapy device 102 may not include either the canister 104 or the filter 122, such that the pump 120 may be directly coupled to the wound site 106 via the tubing 108.

Heat sink 116 may be provided to increase a rate of heat dissipation from therapy device 102 or components thereof, such as pump 120. For example, heat sink 116 can be configured to have a relatively greater coefficient for convective heat transfer than other components of therapy device 102, such as by having a relatively greater surface area to volume ratio. Heat sink 116 may be mounted to control unit 114, pump 120, or a circuit board (not shown) to which control unit 114 and/or pump 120 are mounted. In some embodiments, heat sink 116 includes a plurality of fins.

Control unit 114 can be configured to operate pump 120, valve 118, and/or other controllable components of therapy device 102. In some embodiments, control unit 114 is configured to operate pump 120 by transmitting a control signal to pump 120 via alternating current circuit 140, which includes first arm 142 and second arm 144. The arms 142, 144 may be associated with corresponding pump drive electrodes for pump 120.

In some embodiments, therapy device 102 includes a variety of sensors, which can communicate sensor measurements to control unit 114. For example, therapy device 102 is shown to include a temperature sensor 124 configured to measure a temperature of pump 120 and communicate the measured temperature of pump 120 to control unit 114. Temperature sensor 124 may be a thermocouple.

In some embodiments, NPWT system 100 includes a pressure sensor 126 configured to measure the pressure at wound site 106 and communicate the measured pressure to control unit 114. NPWT system 100 may also include a pressure sensor 132 configured to measure the pressure at the pump, and a resonance sensor 136 configured to measure a resonance of pump 120 (e.g., of the movable member of pump 120). Control unit 114 can use the sensor measurements as inputs to various control operations performed by control unit 114, including adjusting operation of pump 120 based on sensor measurements.

In some embodiments, therapy device 102 includes a user interface 110. User interface 110 may include one or more buttons, dials, sliders, keys, or other input devices configured to receive input from a user. User interface 110 may also include one or more display devices (e.g., LEDs, LCD displays, etc.), speakers, tactile feedback devices, or other output devices configured to provide information to a user. In some embodiments, the pressure measurements recorded by pressure sensors 126 are presented to a user via user interface 110. User interface 110 can also display alerts generated by control unit 114.

In some embodiments, therapy device 102 includes a data communications interface 112 (e.g., a USB port, a wireless transceiver, etc.) configured to receive and transmit data. Communications interface 112 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 112 can include a USB port or an Ethernet card and port for sending and receiving data via an Ethernet-based communications link or network. In another example, communications interface 112 can include a Wi-Fi transceiver for communicating via a wireless communications network or cellular or mobile phone communications transceivers.

FIG. 2 also illustrates sensor system 200 of NPWT system 100. Sensor system 200 includes a first displacement sensor 204 and a second displacement sensor 206. In some embodiments, first displacement sensor 204 is configured to measure a displacement in a first direction (e.g., latitudinal displacement), while second displacement sensor 206 is configured to measure a displacement in a second direction (e.g., longitudinal displacement). The first direction may be substantially perpendicular to the second direction. For example, an angle between the first direction and the second direction may be greater than or equal to 80 degrees and less than or equal to 100 degrees, or any subrange between 80 degrees and 100 degrees. Sensor system 200 can also include a moisture sensor 208 configured to measure a moisture (e.g., fluid, hydration) level in the wound dressing of wound site 106.

Figure 3:
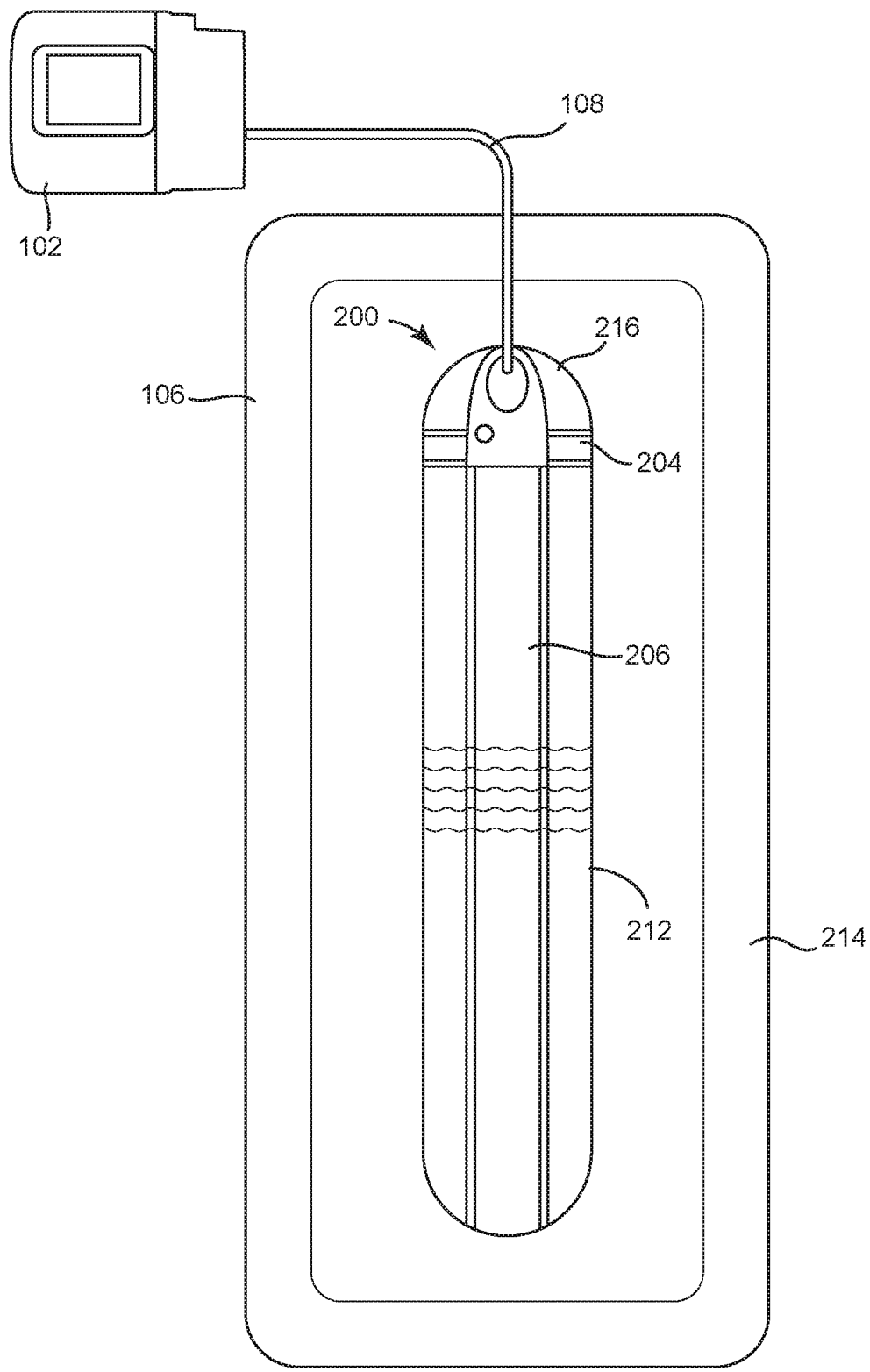
FIG. 3 is a schematic diagram illustrating a sensor system removably coupled to a wound dressing, according an exemplary embodiment.
Figure 4:
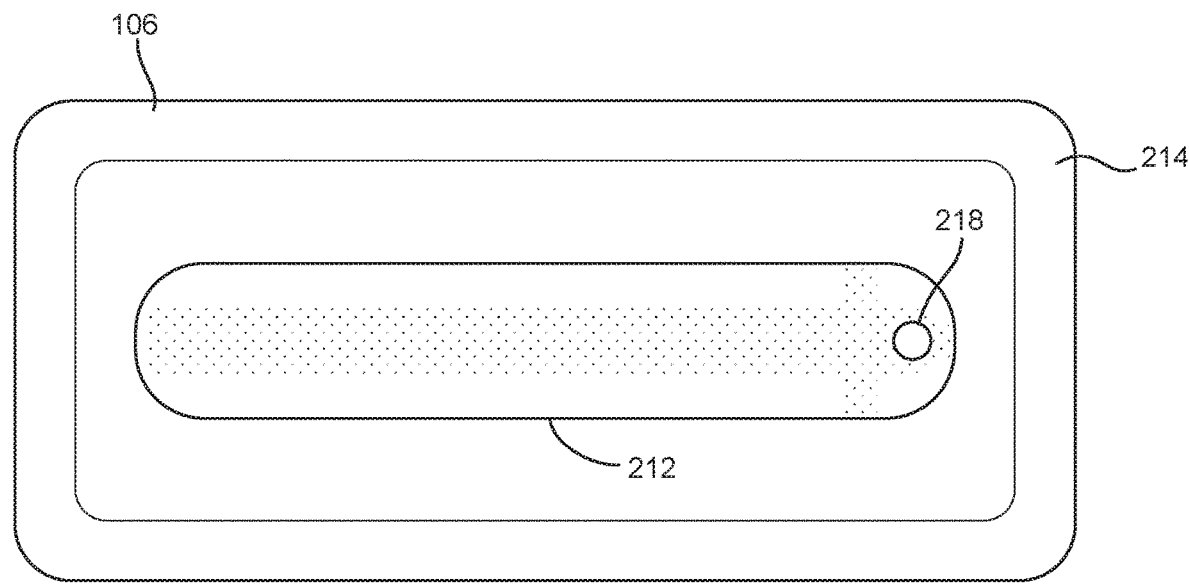
FIG. 4 is a schematic diagram illustrating the wound dressing of FIG. 3 in greater detail, according to an exemplary embodiment.
Figure 5:
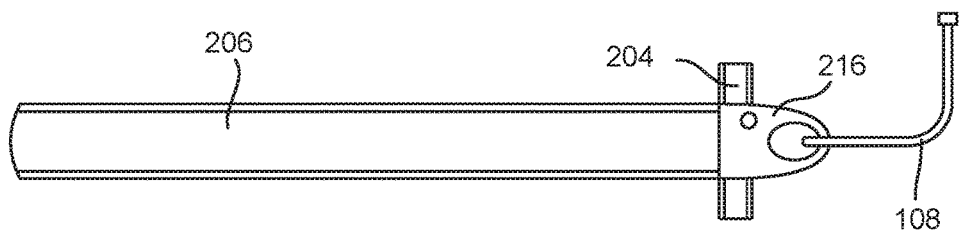
FIG. 5 is a schematic diagram illustrating the sensor system of FIG. 3 in greater detail, according to an exemplary embodiment.

Negative Pressure Wound Therapy Systems with Wound Dressings and Sensor Systems for Measuring Patient Therapy Parameters Referring now to FIGS. 3-5, a schematic diagram illustrating sensor system 200 and wound site 106 in greater detail is shown, according to an exemplary embodiment. A wound dressing 214 is disposed at wound site 106 of the patient. In some embodiments, wound dressing 214 is configured to extend a first length along the first direction, and a second length greater than the first length along the second direction. It will be appreciated that when wound dressing 214 is applied to a wound (which will typically extend primarily in a single wound direction) at wound site 106, wound dressing 214 may generally be aligned with the wound such that the second direction is aligned with the single wound direction.

Wound dressing 214 includes a negative pressure interface 212 and a sensor module 216. Negative pressure interface 212 can be fluidly coupled to wound dressing 214, and to tubing 108, either directly or, as illustrated, via sensor module 216, so that the negative pressure applied from therapy device 102 via tubing 108 is applied to wound dressing 214 (and thus the wound) via negative pressure interface 212. In some embodiments, negative pressure interface 212 is a pad. Wound dressing 214 can be an incisional wound dressing for placement over a closed incision. Wound dressing 214 can include a first layer (e.g., a lower, wound-facing layer), a foam layer (e.g., an elongate foam extending along the second direction), and a cover layer configured to seal wound dressing 214 to skin of the patient at or adjacent to wound site 106. In some embodiments, wound dressing 214 is configured to collapse (e.g., reduce in volume) while negative pressure is applied to wound dressing 214 by pump 120. In some embodiments, wound dressing 214 is configured to apply at least one of a lateral force or a longitudinal force, which may correspond to the negative pressure applied by pump 120 via wound dressing 214. Wound dressing 214 can be sized and shaped for placement over a joint.

In some embodiments, at least one of first displacement sensor 204 or second displacement sensor 206 includes an electro active polymer (EAP) sensor. In response to a displacement of the EAP, the EAP can change in capacitance, and an indication of the change in capacitance can be outputted by the EAP sensor. For example, the EAP sensor can include a dielectric polymer film between two stretchable electrodes; as the dielectric film is stretched or strained, it can change in cross-sectional volume as a function of area and accordingly change in capacitance. In some embodiments, the EAP sensor is an EAP Sensor manufactured by PARKER HANNIFIN CORP of Cleveland, Ohio. At least one of first displacement sensor 204 or second displacement sensor 206 may additionally or alternatively include various other displacement or position sensors, including but not limited to strain gauge sensors and eddy current sensors.

In some embodiments, first displacement sensor 204 measures a latitudinal displacement of wound dressing 214, which can be used to determine a latitudinal apposition force. In some embodiments, second displacement sensor 206 measures a longitudinal displacement of wound dressing 214, which can be used to detect dressing bend and movement, and thus joint movement and degree of movement (e.g., a lower force would indicate a less extensive bend).

In some embodiments, at least one of first displacement sensor 204 or second displacement sensor 206 can detect a force on wound dressing 214. Sensor module 216 and/or therapy device 102 can determine articulation of a joint based on the detected force (or based on displacement). Sensor module 216 can communicate an indication of the articulation to data communications interface 112 of therapy device 102, or to another remote destination. Therapy device 102 can store and/or output the indication of the articulation, including storing a count of received indications of the articulation over time (e.g., store a count on a per-hour, per-day, per-week basis, or any other such periodic basis).

Sensor module 216 can receive sensor measurements from first displacement sensor 204 and from second displacement sensor 206. In some embodiments, sensor module 216 includes communications electronics configured to transmit a sensor signal indicating the received sensor measurements to a remote destination, such as therapy device 102. The communications electronics can be similar to data communications interface 112 of therapy device 102. Sensor module 216 can be used to provide the sensor measurements to therapy device 102 or another remote destination for further processing as described below by control unit 114; additionally, or alternatively, sensor module 216 can perform one or more of the processing functions performed by control unit 114 based on the sensor measurements. Sensor module 216 can include a power source (e.g., battery), which may be rechargeable.

In some embodiments, sensor system 200 includes moisture sensor 208. Moisture sensor 208 can detect a level of moisture in wound dressing 214. Moisture sensor 208 may be implemented by at least one of first displacement sensor 204 or second displacement sensor 206, such as if at least one of first displacement sensor 204 or second displacement sensor 206 include an EAP sensor (as the output of an EAP sensor, based on capacitance changes, can vary as a function of moisture). Moisture sensor 208 may additionally or alternatively be implemented by an EAP sensor separate from at least one of first displacement sensor 204 or second displacement sensor 206. In various such embodiments sensor module 216 can receive a moisture measurement from moisture sensor 208 can be used along with sensor measurement(s) from at least one of first displacement sensor 204 or second displacement sensor 206, and use the moisture measurement to correct the sensor measurement(s) from at least one of first displacement sensor 204 or second displacement sensor 206 for the effect of moisture, which can enable more accurate determination of displacement and/or appositional force. In some embodiments, from at least one of first displacement sensor 204 or second displacement sensor 206 is at least partially enclosed in a housing, which can separate at least one of first displacement sensor 204 or second displacement sensor 206 from moisture in wound dressing 214 that could otherwise affect the sensor measurements for displacement. In some embodiments, a moisture measurement from moisture sensor 208 (or sensor measurements from sensors 204, 206) can be used to measure at least one of fluid level or fluid flow rate through wound dressing 214.

Moisture sensor 208 can be particularly positioned to detect moisture about the wound at wound site 106. For example, moisture sensor 208 can be positioned within a threshold proximity of the second surface of wound dressing 214 (the surface to be placed adjacent to the wound) to enable moisture sensor 208 to detect moisture at the perimeter of the wound. The threshold proximity may correspond to a distance at which a desired signal quality for detecting moisture from the wound is achieved. A moisture measurement from such a moisture sensor 208 can be used to identify potential wound maceration.

As shown in FIGS. 3-5, sensor system 200 (e.g., sensors 204, 206, sensor module 216, and/or tubing 108) can be removably coupled to wound dressing 214. Sensor system 200 can be removably attached to a first surface of wound dressing 214 opposite a second surface at which wound dressing 214 faces the wound, such as to fluidly couple tubing 108 to negative pressure interface 212 via opening 218. As such, sensor system 200 can be reused while wound dressing 214 is replaced.

In some embodiments, wound dressing 214 includes an adhesive to removably couple wound dressing 214 to sensor system 200. The adhesive may be light activated. For example, the adhesive may be covered by a light blocking layer, which when removed, exposes the adhesive to cause the adhesive to transition from a relatively non-adhesive state to a relatively adhesive state. The adhesive may be activated by light of a specific wavelength or wavelength bandwidth, such as ultraviolet (UV) light, such that the adhesive can be selectively activated using an activation device configured to output light of the specific wavelength or wavelength bandwidth.

In some embodiments, wound dressing 214 includes at least one attachment member configured to attach to sensor system 200, including but not limited to a latch, a twist latch, or a snap fit. In some embodiments, the at least one attachment member includes a first attachment member and a second attachment member spaced from the first attachment member by a distance greater than a threshold distance sufficient to apply tension to second displacement sensor 206 when second displacement sensor 206 is coupled to wound dressing 214.

In some embodiments, sensor system 200 includes at least one position sensor, such as an accelerometer. The accelerometer can be used to provide additional displacement data regarding movement of wound dressing 214, such as displacement data for different directions/degrees of freedom than sensors 204, 206.

Figure 6:
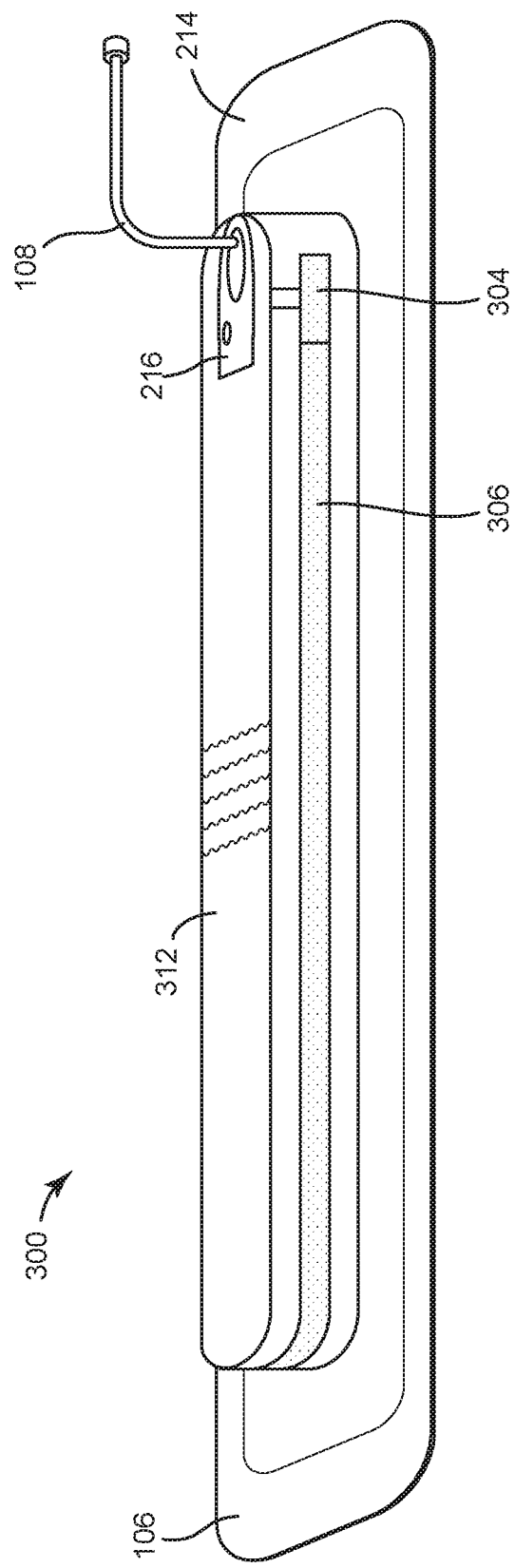
FIG. 6 is a schematic diagram illustrating a sensor system disposed within a wound dressing, according to an exemplary embodiment.

Referring now to FIG. 6, a schematic diagram illustrating a sensor system 300 is shown, according to an exemplary embodiment. Sensor system 300 is similar to sensor system 200, except that the sensor components are designed to be integrated with the wound dressing. As shown in FIG. 6, negative pressure interface 312 is attached to wound dressing 214, and wound dressing 214 is disposed at wound site 106. Negative pressure interface 312 is similar to negative pressure interface 212. Negative pressure interface 312 includes first displacement sensor 304 and second displacement sensor 306, which are each disposed within negative pressure interface 312. First displacement sensor 304 can incorporate features of first displacement sensor 204 (e.g., first displacement sensor 304 can be an EAP sensor), and second displacement sensor 306 can incorporate features of second displacement sensor 206 (e.g., second displacement sensor 306 can be an EAP sensor). Similar to sensor system 200, sensor system 300 may include additional sensors, such as a moisture sensor. In some embodiments, while sensors 304, 306 are integrated with negative pressure interface 312, sensor module 216 may be removably coupled to negative pressure interface 312, which can enable sensor module 216 to be removed and re-used across dressings.

Control Unit

Figure 7:
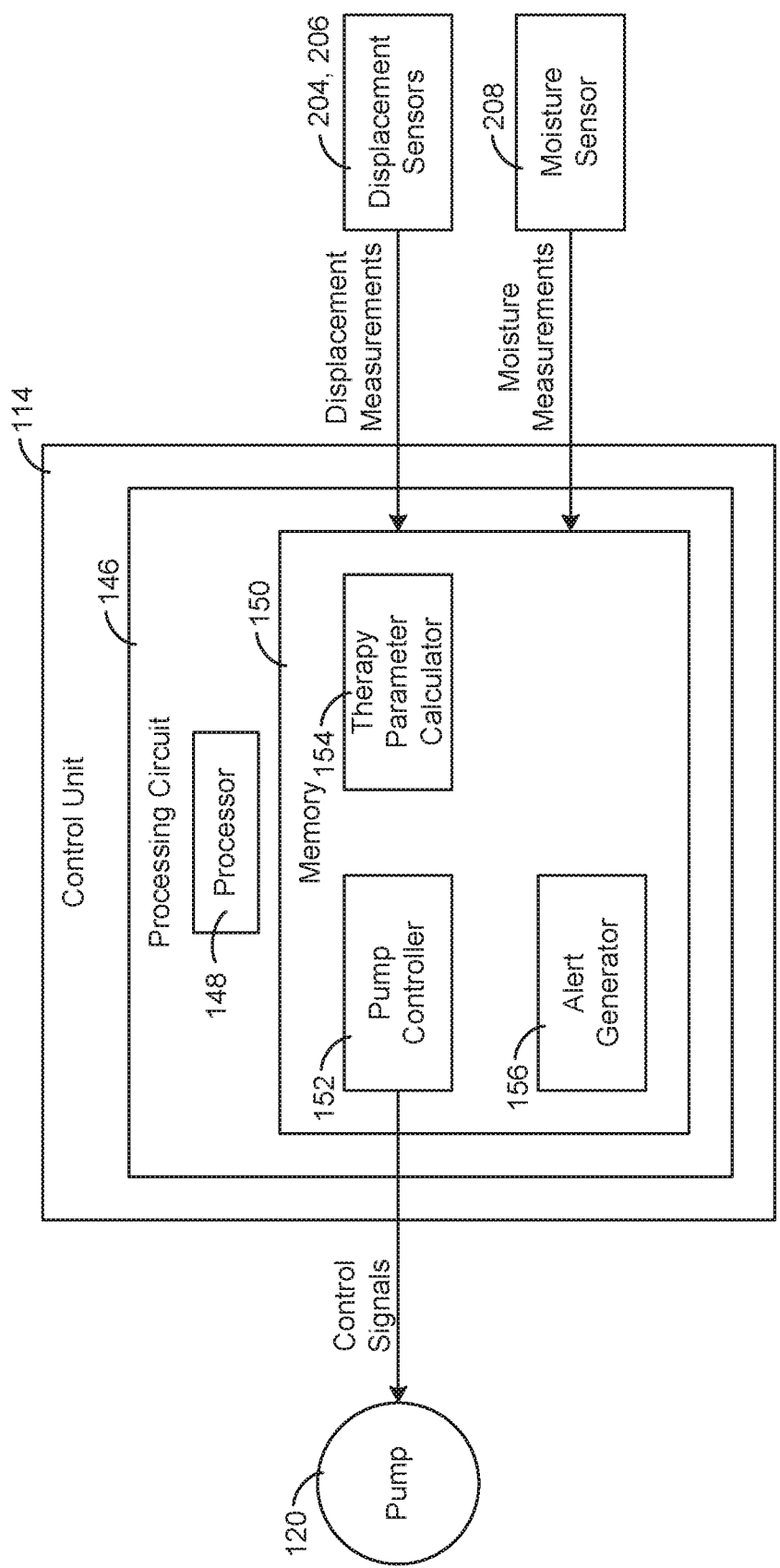
FIG. 7 is a block diagram of a control unit of the NPWT device of FIG. 1, according to an exemplary embodiment.

Referring now to FIG. 7, a block diagram illustrating control unit 114 in greater detail is shown, according to an exemplary embodiment. Control unit 114 can be used with various wound dressings and sensor systems described herein, including sensor systems 200, 300. Control unit 114 is shown to include a processing circuit 146 including a processor 148 and memory 150. Processor 148 may be a general purpose or specific purpose processor, an application specific integrated circuit (ASIC), one or more field programmable gate arrays (FPGAs), a group of processing components, or other suitable processing components. Processor 148 is configured to execute computer code or instructions stored in memory 150 or received from other computer readable media (e.g., CDROM, network storage, a remote server, etc.).

Memory 150 may include one or more devices (e.g., memory units, memory devices, storage devices, etc.) for storing data and/or computer code for completing and/or facilitating the various processes described in the present disclosure. Memory 150 may include random access memory (RAM), read-only memory (ROM), hard drive storage, temporary storage, non-volatile memory, flash memory, optical memory, or any other suitable memory for storing software objects and/or computer instructions. Memory 150 may include database components, object code components, script components, or any other type of information structure for supporting the various activities and information structures described in the present disclosure. Memory 150 may be communicably connected to processor 148 via processing circuit 146 and may include computer code for executing (e.g., by processor 148) one or more processes described herein. When processor 148 executes instructions stored in memory 150, processor 148 generally configures control unit 114 (and more particularly processing circuit 146) to complete such activities. It will be appreciated that some or all the functions executed by control unit 114 may be executed by sensor module 216 and/or a remote computing device, such as a device for use by a clinician that is communicatively coupled to sensor module 216 and/or therapy device 102.

Control unit 114 is shown to include a pump controller 152. Pump controller 152 generates control signals to control operation of pump 120. Pump controller 152 can configure parameters of the control signals, such as current, voltage, frequency, amplitude, or intermittency. In some embodiments, pump controller 152 generates alternating current control signals having a root mean square (RMS) voltage, and transmits the control signals to pump 120 via alternating current circuit 140. For example, pump controller 152 can generate the control signals to have a particular RMS voltage by modulating a first phase angle of a first signal component associated with first arm 142 relative to a second phase angle of a second signal component associated with second arm 144.

Control unit 114 is shown to include a therapy parameter calculator 154. Therapy parameter calculator 154 can receive sensor measurements from various sensors coupled to therapy device 102, such as displacement measurements from displacement sensors 204, 206, and moisture measurements from moisture sensors 208.

Each of sensors 204, 206, 208 may be EAP sensors that output a sensor measurement in a sensor-specific unit of measure, such as capacitance or a voltage representative of capacitance; therapy parameter calculator 154 can be configured to convert the received sensor measurement to displacement, moisture level, fluid level, or fluid flow rate as appropriate. For example, therapy parameter calculator 154 can store calibration functions that when executed, convert sensor measurements from sensors 204, 206, 208 to appropriate units of measure.

Therapy parameter calculator 154 can calculate one or more therapy parameters based on received sensors measurements. For example, therapy parameter calculator 154 can receive a first displacement measurement indicating a first displacement of first displacement sensor 204, and calculate the therapy parameter based on the first displacement measurement (or similarly based on a second displacement measurement from second displacement sensor 206).

In some embodiments, the therapy parameter includes an appositional force. For example, therapy parameter calculator 154 can receive a first displacement measurement from first displacement sensor 204, and execute a latitudinal apposition force function to calculate a latitudinal apposition force corresponding to the first displacement measurement. Therapy parameter calculator 154 can receive a second displacement measurement from second displacement sensor 206, and execute a longitudinal apposition force function to calculate a longitudinal apposition force corresponding to the second displacement measurement. Therapy parameter calculator 154 can also calculate at least one of a degree of movement or a frequency of movement of a joint adjacent to wound site 106 based on the second displacement measurement. For example, a lesser longitudinal force may be indicative of a lesser joint bend.

Pump controller 152 can control operation of pump 120 based on therapy parameters calculated by therapy parameter calculator 154. For example, pump controller 152 can compare an appositional force therapy parameter (e.g., latitudinal apposition force) to a target appositional force to calculate a difference between the appositional force therapy parameter and the target appositional force, and modify a pressure applied to wound site 106 using pump 120 to reduce the difference. As such, control unit 114 can be used to directly control the effectiveness of negative pressure wound therapy based on appositional force, rather than using pressure or other variables as a proxy measure of therapy effectiveness. In some embodiments, pump controller 152 receives a control command from a remote source and controls operation of pump 120 based on the received control command Alert generator 156 can generate alerts based on the calculated therapy parameters. Alert generator 156 can compare the therapy parameter to a predetermined threshold condition including at least one of a minimum threshold or a maximum threshold, and output an alert responsive to the therapy parameter not satisfying the predetermined threshold condition. Alert generator 156 can to store the alert. The predetermined threshold condition may be associated with therapy parameters including but not limited to latitudinal apposition force, longitudinal apposition force, joint movement, and wound dressing fluid levels.

Alert generator 156 can cause data communications interface 112 to transmit the alert to a remote destination. Alert generator 156 can also be used to transmit sensor measurements to the remote destination, to enable remote monitoring of therapy status. For example, alert generator 156 can generate alerts indicative of sensor measurements which can be used to determine therapy compliance and patient ambulatory activity. Alert generator 156 can be used to transmit alerts and/or sensor measurement in response to a remote request from therapy unit 102 (e.g., via user interface 110) or a remote device (e.g., a device operated by a clinician that is communicatively coupled to control unit 114).

In some embodiments, alert generator 156 can generate an alert indicative of a leak. Alert generator 156 can compare a calculated appositional force value to a target appositional force value, and determine that the target appositional force value is satisfied responsive to a difference between the calculated appositional force value and the target appositional force value being less than a threshold difference. Responsive to determining the target appositional force value being satisfied, alert generator 156 can compare a duty cycle of operation of pump 120 by pump controller 152 to a threshold duty cycle. The threshold duty cycle can be indicative of an expected pump operation level during normal and/or steady state operation. Responsive to the duty cycle being greater than the threshold duty cycle, alert generator 156 can determine a leak condition to be present (e.g., the duty cycle may indicate that pump 120 is being driven harder than expected once the target appositional force has been achieved), and generate the alert indicative of the leak.

Alert generator 156 can generate an alert indicative of wound dressing misalignment (e.g., misapplication). In some embodiments, alert generator 156 uses the duty cycle of pump 120 and the measured appositional value to determine wound dressing misalignment. For example, alert generator 156 can compare the duty cycle to the threshold duty cycle. Alert generator 156 can initiate a timer responsive to the duty cycle being greater than the threshold duty cycle (and reset the timer responsive to the duty cycle falling below the threshold duty cycle). Alert generator 156 can compare a time outputted by the timer to a threshold time (which may include a delay to account for high duty cycle operation at the start of pump 120 operation for dressing draw down). If the time is greater than the threshold time, alert generator 156 can compare the appositional force to the target appositional force. As such, responsive to determining that (1) the time is greater than the threshold time, and (2) the appositional force is less than the target appositional force, alert generator 156 can generate an alert indicative of dressing misalignment.

Alert generator 156 can generate an alert indicative of movement of a joint of the patient. For example, alert generator 156 can receive an indication of an articulation of the joint. Alert generator 156 can determine whether a count of received indications (e.g., for a predetermined period of time, such as an hour, day, week, month, year, or any range therein) satisfies a compliance condition. The compliance condition may include at least one of a first threshold count of received indications to be exceeded or a second threshold count of received indications to not be exceeded. Alert generator 156 can compare the count of received indications to the at least one of the first threshold or the second threshold, determine the patient to be in compliance with the compliance condition responsive to the count being at least one of greater than or equal to the first threshold or less than or equal to the second threshold, otherwise determine the patient to not be in compliance with the compliance condition responsive to the count being at least one of less than the first threshold (if alert generator 156 evaluates the compliance condition using the first threshold) the compliance condition includes the first threshold) or greater than the second threshold (if alert generator 156 evaluates the compliance condition using the second threshold). Alert generator 156 can output the alert indicative of movement using user interface 110 and/or transmit the alert to a remote destination, such as a remote device operated by caregiver in order to inform the caregiver of the treatment compliance/non-compliance. In some embodiments, alert generator 156 modifies (e.g., increases) at least one of the at least one of the first threshold or the second threshold responsive to a second predetermined period of time expiring, which can enable therapy system 100 to adjust therapy over time. second predetermined period of time can be greater than or equal to a day and less than or equal to a week.

Control Processes

Figure 8:
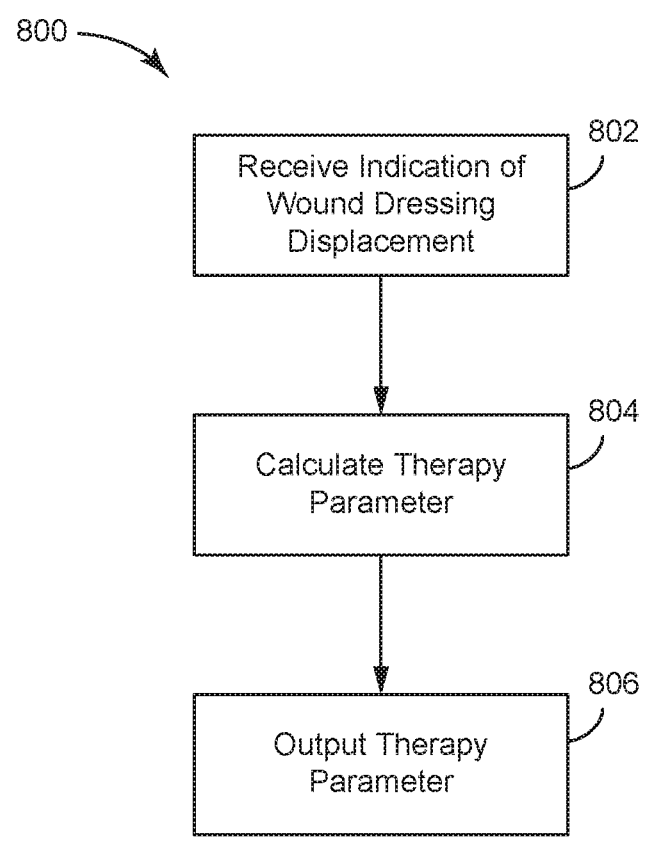
FIG. 8 is a flowchart of a process for operating the sensor system and NPWT device of FIG. 1, according to an exemplary embodiment.

Referring now to FIG. 8, a flowchart of a process 800 for operating a sensor system associated with a negative pressure wound therapy (NPWT) device is shown, according to an exemplary embodiment. Process 800 can be performed by one or more components of sensor system 200, sensor system 300, and/or NPWT system 100, as described with reference to FIGS. 1-7. For example, process 800 can be performed by sensor system 200 and therapy device 102 using control unit 114 to control pump 120 based on sensor measurements received from sensor system 200.

Process 800 is shown to include receiving an indication of a displacement of a wound dressing for a wound of a patient (step 802). The indication can be received from at least one sensor, which may include at least one electro-active polymer (EAP) sensor. The at least one EAP sensor can be coupled to the wound dressing. The at least one EAP sensor can be configured to output the indication based on a change in capacitance of the at least one EAP sensor corresponding to the displacement. In some embodiments, the at least one EAP sensor includes a first EAP sensor configured to detect a latitudinal displacement and a second EAP sensor configured to detect a longitudinal displacement. The at least one sensor may include one or more accelerometers. The at least one sensor may be removably attached to the wound dressing or disposed within the wound dressing.

Process 800 is shown to include calculating a therapy parameter corresponding to the indication of the displacement (step 804). The therapy parameter can include at least one of an appositional force that the wound dressing applies to the wound of the patient or a movement of a joint of the patient about the wound dressing, including a degree or frequency of movement, joint articulation, or an indication of a movement beyond a threshold degree or frequency. In some embodiments, the therapy parameter includes a moisture level, fluid level, fluid flow, or other parameter indicative of hydration or change in hydration of the wound dressing.

Process 800 is shown to outputting the calculated therapy parameter (step 806). Outputting the therapy parameter may include transmitting the indication of the displacement to at least one of the NPWT device or another remote electronic device. Outputting the therapy parameter may include storing the therapy parameter in memory for later retrieval. Outputting the therapy parameter may include comparing the therapy parameter to a predetermined threshold condition including at least one of a minimum threshold or a maximum threshold, and outputting an alert responsive to the therapy parameter not satisfying the predetermined threshold condition.

In some embodiments, operation of the NPWT device is modified using the therapy parameter. The therapy parameter may include an appositional force. A difference can be calculated between the appositional force and a target appositional force value, and a pressure applied by the wound dressing to the wound (using the NPWT device) can be modified to reduce the difference.

In some embodiments, a level of moisture in the wound dressing is detected. The level of moisture can be compared to a predetermined threshold moisture condition including at least one of a minimum moisture threshold or a maximum moisture threshold. An alert can be outputted responsive to the level of moisture not satisfying the predetermined threshold moisture condition.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy system, comprising:
   a wound dressing for a wound of a patient;
   a first sensor configured to be coupled to the wound dressing, the first sensor configured to output an indication of a displacement in a first direction of the wound dressing;
   a second sensor configured to be coupled to the wound dressing, the second sensor configured to output an indication of a displacement in a second direction of the wound dressing, the second direction perpendicular to the first direction;
   wherein the wound dressing is configured to extend a first length along the first direction and a second length greater than the first length along the second direction; and
   a control circuit configured to:
      receive the indication of the displacement in the first direction and the indication of displacement in the second direction of the wound dressing,
      calculate a therapy parameter including at least an appositional force of the wound dressing corresponding to the indication of the displacement in the first direction and a longitudinal movement of the wound dressing corresponding to the indication of displacement in the second direction, and
      output the therapy parameter.

2. The negative pressure wound therapy system of claim 1, wherein the wound dressing is configured to apply the appositional force to the wound of the patient.

3. The negative pressure wound therapy system of claim 2, wherein the control circuit is further configured to calculate a difference between the appositional force and a target appositional force value and modify a pressure applied by the wound dressing to the wound to reduce the difference.

4. The negative pressure wound therapy system of claim 1, wherein the wound dressing is an incisional wound dressing for placement over a closed incision, and wherein the second length of the wound dressing is configured to extend along the closed incision.

5. The negative pressure wound therapy system of claim 1, wherein the wound dressing comprises a lower, wound facing layer, an elongate foam, and a cover layer for sealing the wound dressing to a patient's skin.

6. The negative pressure wound therapy system of claim 5, wherein the wound dressing collapses under negative pressure and applies at least one of a lateral force or a longitudinal force.

7. The negative pressure wound therapy system of claim 1, wherein the first sensor includes a first electro active polymer (EAP) sensor and the second sensor includes a second EAP sensor, and wherein the indication of the displacement in the first direction and the indication of the displacement in the second direction of the wound dressing is based upon a change in a capacitance of at least one of the first EAP sensor or the second EAP sensor.

8. The negative pressure wound therapy system of claim 1, wherein the control circuit is configured to compare the therapy parameter to a predetermined threshold condition including at least one of a minimum threshold or a maximum threshold, and output an alert responsive to the therapy parameter not satisfying the predetermined threshold condition.

9. The negative pressure wound therapy system of claim 1, further comprising a moisture sensor configured to detect a level of moisture in the wound dressing, wherein the control circuit is further configured to compare the level of moisture to a predetermined threshold moisture condition including at least one of a minimum moisture threshold or a maximum moisture threshold, and output an alert responsive to the level of moisture not satisfying the predetermined threshold moisture condition.

10. The negative pressure wound therapy system of claim 1, wherein at least one of the first sensor and the second sensor is configured to measure at least one of a fluid level or a fluid flow rate through the wound dressing.

11. The negative pressure wound therapy system of claim 1, wherein the control circuit is coupled to a communications circuit, the communications circuit configured to transmit the therapy parameter to a remote electronic device.

12. A method, comprising:
receiving an indication of a displacement in a first direction of a wound dressing for a wound of a patient from a first electro-active polymer (EAP) sensor;
receiving an indication of a displacement in a second direction of a wound dressing from a second EAP sensor, the second direction perpendicular to the first direction, the first EAP sensor extending along a first length of the wound dressing along the first direction and the second EAP sensor extending along a second length of the wound dressing along the second direction that is greater than the first length, the first EAP sensor and the second EAP sensor configured to output the indication based on a change in capacitance of the first EAP sensor and the second EAP sensor corresponding to the displacement in the first direction and the displacement in the second direction;
calculating a therapy parameter including at least an appositional force of the wound dressing corresponding to the indication of the displacement in the first direction and a longitudinal movement of the wound dressing corresponding to the indication of displacement in the second direction; and
outputting the therapy parameter.

13. The method of claim 12, wherein the wound dressing is configured to apply the appositional force to the wound of the patient.

14. The method of claim 13, the method further comprising calculating a difference between the appositional force to a target appositional force value and modifying a pressure applied by the wound dressing to the wound to reduce the difference.

15. The method of claim 12, further comprising comparing the therapy parameter to a predetermined threshold condition including at least one of a minimum threshold or a maximum threshold, and outputting an alert responsive to the therapy parameter not satisfying the predetermined threshold condition.

16. The method of claim 12, further comprising transmitting the indication of the displacement in the first direction and the indication of the displacement in the second direction to at least one of a negative pressure wound therapy device configured to apply a vacuum to the wound dressing or a remote electronic device.

17. The method of claim 16, wherein the indication of the displacement in the first direction and the indication of the displacement in the second direction is transmitted to the remote electronic device, the method further comprising using the remote electronic device to perform at least one of outputting the indication of the displacement in the first direction and the indication of the displacement in the second direction, calculating the therapy parameter, or outputting the therapy parameter, the therapy parameter being indicative of whether the patient is moving more or less than a desired movement subsequent to a surgery.

* * * * *